United States Patent
McGuinness et al.

(10) Patent No.: US 6,797,512 B1
(45) Date of Patent: Sep. 28, 2004

(54) SELECTION SYSTEM FOR GENERATING EFFICIENT PACKAGING CELLS FOR LENTIVIRAL VECTORS

(75) Inventors: Ryan McGuinness, Oakland, CA (US); Luigi Naldini, Turin (IT)

(73) Assignee: Cell Genesys, Inc., Foster City, CA (US)

(*) Notice: Subject to any disclaimer, the term of this patent is extended or adjusted under 35 U.S.C. 154(b) by 0 days.

(21) Appl. No.: 09/831,623

(22) PCT Filed: Nov. 12, 1999

(86) PCT No.: PCT/US99/24018

§ 371 (c)(1),
(2), (4) Date: Sep. 12, 2001

(87) PCT Pub. No.: WO00/29421

PCT Pub. Date: May 25, 2000

Related U.S. Application Data

(60) Provisional application No. 60/108,169, filed on Nov. 13, 1998.

(51) Int. Cl.[7] .............................................. C12N 15/00
(52) U.S. Cl. .................. 435/320.1; 536/23.1; 536/23.4; 536/23.72; 536/24.1; 536/24.2
(58) Field of Search ...................... 435/320.1; 536/23.1, 536/23.4, 23.72, 24.1, 24.2

(56) References Cited

U.S. PATENT DOCUMENTS

| | | |
|---|---|---|
| 5,693,508 A | 12/1997 | Chang |
| 5,716,613 A | 2/1998 | Guber et al. |
| 5,716,826 A | 2/1998 | Gruber et al. |
| 5,739,118 A | 4/1998 | Carrano et al. |
| 5,747,307 A | 5/1998 | Lever et al. |

FOREIGN PATENT DOCUMENTS

| | | |
|---|---|---|
| WO | WO 93/17118 | 9/1993 |
| WO | WO 98/39463 | 9/1998 |

OTHER PUBLICATIONS

Kaul et al. Regulated lentiviral packaging cell line devoid of most viral cis–acting sequences. Virology (Sep. 1998) vol. 249, No. 1, pp. 167–174.*

Ory, Daniel S. et al., "A stable human–derived packaging cell line for production of high titer retrovirus/vesicular stomatitis virus G pseudotypes," Proc. Natl. Acad. Sci., USA, vol. 93, Oct. 1996, pp. 11400–11406.

Schneider, Ralf et al., "Inactivation of the Human Immuno–deficiency Virus Type 1 Inhibitory Elements Allows Rev–Independent Expression of Gag and Gag/Protease and Particle Formation," Journal of Virology, vol. 71, No. 7, Jul. 1997, pp. 4892–4903.

Yu et al., "Inducible Human Immunodeficiency Virus Type 1 Packaging Cell Lines," Jnl of Virology, 1996, 70(7): 4530–4537.

* cited by examiner

*Primary Examiner*—Ulrike Winkler
(74) *Attorney, Agent, or Firm*—Linda R. Judge; Gates & Cooper LLP

(57) ABSTRACT

A method for selecting packaging cells that express high levels of gag/pol is provided.

7 Claims, 3 Drawing Sheets pMDH L g/p RRE Spl CD4

CMV enpo: human CMV immediate early enhancer and promoter
Major 5' SD: HIV 5' splice donor
gag/pol: HIV gag and pol coding regions
RRE: HIV Rev Responsive Element
SA: HIV tat 3rd exon splice acceptor region
CD4: Human CD4 coding region
pA: Rat insulin poly adenylation site

SELECTION SYSTEM FOR GENERATING EFFICIENT PACKAGING CELLS FOR LENTIVIRAL VECTORS This application claims benefit of 60/108,169, filed Nov. 13, 1998.

BACKGROUND OF THE INVENTION

Generation of efficient packaging cell lines for lentiviral vectors is hampered by the cytotoxicity of some of the products of the gag and pol genes. Thus, it is desirable to have inducible expression of gag and pol so that optimal clones that will express gag and pol at high levels when needed can be selected in the absence of gag/pol expression.

SUMMARY OF THE INVENTION

A method for selecting cells which express gag and pol and thus are useful as packaging cells is obtained by linking a selectable marker to the gag/pol expression cassette of a packaging vector in such a way that the marker is expressed by the same promoter which controls expression of the gag/pol genes although expression of the gag/pol genes is suppressed. Efficient expression of the marker predicts efficient expression of the gag/pol genes on induction.

DETAILED DESCRIPTION OF THE INVENTION

Figure 1:
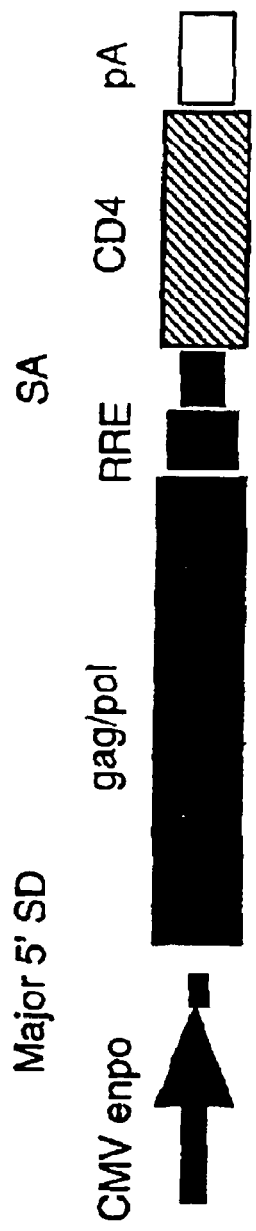
FIG. 1 depicts a recombinant vector which exemplifies the instant invention. The gag/pol sequences are flanked by splice donor and splice acceptor sites. Also contained within the splice donor and splice acceptor sites is an RRE (Rev responsive element).

The invention takes advantage of the splicing control mechanisms of HIV and other lentiviruses which regulate expression of the late viral genes, gag/pol and env, by means of a cis acting RNA element, RRE, and a trans acting regulatory protein, Rev. By the strategic placement of splice control elements, a switch in a gag/pol expression construct allows expression of a downs selectable marker gene in the basal state and of the upstream gag/pol genes only on induction. As both genes are driven by the same constitutive promoter, operation of the switch allows for gag/pol induction to an expression level related to that of the selectable marker.

Three features operate the switch: 1) the gal genes are contained within a splice donor site and one or more splice acceptor sites, wherein the sequences of the acceptor sites do not match the optimal consensus splice acceptor sequence (Lewin, "Genes", John Wiley & Sons, NY) upstream of the marker gene; 2) the gag/pol genes contain sequences which antagonize the expression of gag/pol (Schneider et al., J. Virol. 71:4892–4903, 1997; Schwartz et al., J. Virol. 66:7176–7182, 1992); and 3) the gag/pol genes are linked in cis to the RRE element as well as being separated from the Rev coding sequence.

A promoter which controls the expression of both gag/pol and the marker gene is situated operably thereto, generally upstream from the gag/pol sequences.

The RRE/Rev regulatory system is found in lentiviruses and thus, that of HIV-1 or any other lentivirus can be used. Also, any other trans complementing regulatory system which results in selective splicing which would control the expression of gag/pol as described herein can be used in the practice of the instant invention.

The first two features combine to suppress gag/pol expression in the basal state. The third feature allows for Rev-dependent stimulation, i.e., induction, of the export of unspliced RNA and consequent expression of the gag/pol genes.

Regarding the splice sites, a combination of an efficient splice donor site, such as that of the 5' major splice donor of HIV, and one or more splice acceptor sites, wherein the splice acceptor sites do not match exactly the optimal consensus, are used. Therefore, the splice acceptors of interest are those an artisan would recognize as not being that efficient, strong or good. Nevertheless, the splice acceptor sites are operable, albeit at a suboptimal rate of efficiency. The suboptimal splice sites appear to allow for more efficient expression from spliced transcripts by the Rev-RRE system. An example of such a suboptimal splice acceptor site is that of the third exon of the HIV-1 tat and rev genes.

Non-lentivirus splice donor and splice acceptor sites also can be used in the practice of the instant invention so long as the splicing, and hence expression, of the gag/pol genes is controlled by the presence of a trans acting factor, such as Rev.

The intrinsic instability of the lentiviral gag/pol coding sequences, and particularly the sequences contained in the intron, counteracts expression in the basal state from unspliced transcripts that may accumulate due to the suboptimal nature of the splice sites. Any sequence which is known to be associated with the instability of transcripts can be used in the practice of the instant invention. Instability sequences, however, such as those identified described in Schneider et al. and Schwartz et al., supra, in the gag/pol sequence, may not be strictly required for the operation of the switch.

Any of a number of possible selectable markers can be used. Markers which are readily detectable are desirable. For example, the marker may be a cell surface molecule, which is antigenic, such as a CD molecule or lymphocyte antigen, or a light-emitting molecule, such as green fluorescent protein. An artisan is free to select a selectable marker of interest from those known in the art.

The methods for cloning the various elements of the instant invention into a vector of interest are known in the art.

As a means of introducing yet another level of regulation, expression of the trans acting splice regulatory elements, in the case of HIV-1, Rev, can be inducible as well. In the presence of a separate inducible Rev expression construct, the expression of the gag/pol genes becomes inducible. For example, expression of Rev can be inducible using the tetracycline dependent regulatory system of Ory et al. (Proc.

Natl. Acad. Sci. 93:11400–11406, 1996) wherein Rev is subcloned adjacent to a tet operator. In the presence of tet, Rev is not expressed. However, when tet is withdrawn from the medium, Rev expression occurs.

Other known regulatory elements can be used as known in the art Thus, a suitable and known promoter can be place operably in the construct to regulate expression of the gag/pol and marker genes. Other regulatory elements, such as a polyadenylation site can be used as desired.

Moreover, various modifications can be made to any one element included in the vectors of interest to remove undesirable activities or to enhance desired activities. The artisan can rely on the known activities of the elements contemplated and can practice known techniques to effect the desired changes, for example, deletion of sequences by selective subcloning, inactivation of a gene by site directed mutagenesis and so on.

An advantage of the instant invention is selection of optimal packaging clones for vectors, such as lentiviral-derived, and particularly, HIV-derived, vectors. Using a surface marker for the linked selection, a population of stable, high-level expressors can be sorted on transfection of the constructs, and subsequently as often as needed to maintain performance. In previously described linked-selection systems, expression of the marker gene is coupled to the expression of the desired gene and cannot be operated in the reverse direction.

The instant method also can be used to select packaging clones for lentiviral vectors other than HIV-1, either using the HIV-1 Rev-RRE system, or homologous elements of other lentivirus, so long as the homologous regulatory elements functionally operate equivalently to yield selectable splicing of the gag/pol sequence in the presence of an inducer molecule located in trans to the coding sequences of interest.

The invention now will be exemplified in the following non-limiting examples.

EXAMPLES

A packaging vector, pMDH L g/p RRE Spl CD4 (FIG. 1) was constructed to include the following: immediate/early enhancer/promoter of the human cytomegalovirus (CMV); HIV major 5' splice donor, HIV gag/pol coding regions with optimised translation initiation sequence fitting the Kozak consensus sequence (Dull et al. J. Virol. 72:8463–8471, 1998); HIV RRE element; HIV splice acceptor sites from the $3^{rd}$ exon of tat and rev; human CD4 coding region; and rat insulin poly-adenylation sequence.

Figure 2:
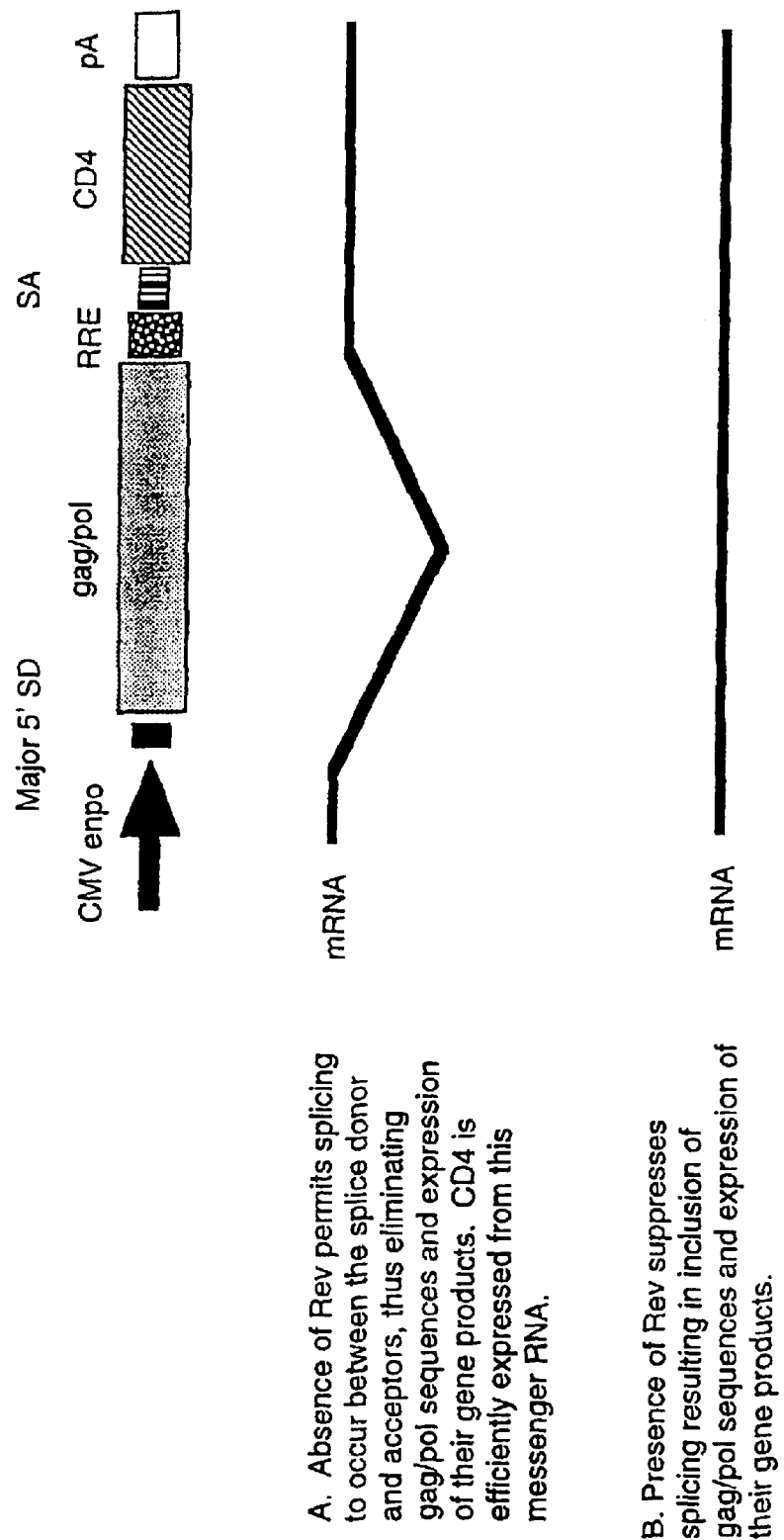
FIG. 2 depicts the mechanism by which a vector containing an RRE would provide inducible expression of only the marker gene, in the case of the exemplary recombinant vector of FIG. 1, the marker is CD4. In the absence of Rev, splicing occurs between the splice donor and splice acceptor sites thereby eliminating the gag/pol sequence. Only CD4 is expressed. When Rev is present, splicing does not occur and the gag/pol genes are expressed.

The lentiviral packaging vector pMDH L g/p RRE Spl CD4 allows for selection of high level expression of the surface marker CD4 with very low expression of the HIV-1 gag/pol genes. Due to the linkage of the CD4 marker to the gag/pol genes, high expression of CD4 correlates with high inducible expression of gag/pol. In the absence of HIV Rev, splicing of the gag/pol sequences between the HIV splice donor and acceptors yield efficient expression of CD4 without appreciable expression of gag and pol (FIG. 2A). In the presence of Rev, the RRE-mediated export of unspliced gag/pol message allows expression of the gag pol proteins (FIG. 2B).

The pMDH L g/p RRE Spl CD4 plasmid was transfected into 293T (Dull et al., supra) with or without a Rev expression plasmid (Dull et al., supra) and with a combination of other plasmids required to generate lentiviral vector delivery of a selectable marker, green fluorescent protein (GFP).

About $4 \times 10^6$ 293T cells were plated per 10 cm dish the night prior to transfection $CaPO_4$ co-transfection of the following plasmids was performed: pMDH L g/p RRE Spl CD4, 7 μg (HIV-derived gag/pol expression plasmid); pRSV Rev, 2.5 μg; pCMV tat, 1 μg; pMD VSVG env, 3.5 μg; and pRRLhPGKGFPSIN-18, 10 μg (a self-inactivating HIV-derived transfer vector carrying a green fluorescent protein coding sequence linked to a PGK promoter). Identical transfections also were performed without the pRSV Rev plasmid, and with the parental packaging vector pMD L g/p RRE in place of pMDH L g/p RRE Spl CD4. Twenty hours after transfection, fresh medium was added and 24 hours later, conditioned medium was harvested for measuring the content of the HIV gag product, p24, by immunocapture (Dupont) and for assaying transduction. The transfected cells were harvested, incubated with phycoerythrin-labelled anti-CD4 antibodies and analyzed by FACS for phycoerythrin and GFP fluorescence.

The transfectants were analyzed for expression of both CD4 and GFP, with and without HIV Rev. In both cases the vast majority of cells were doubly positive for CD4 and GFP. As expected, the average expression level of CD4 was higher in cells not expressing Rev. Expression of basal levels CD4 in the presence of Rev is due to the fact that Rev does not prevent completely the splicing of RRE-containing transcripts.

Similar transfections also were performed with the parental packaging vector pMD L g/p RRE in place of pMDH L g/p RRE Spl CD4. The vector pMD L g/p RRE expresses gag/pol of HIV in a Rev-dependent manner downstream of a constitutively spliced intron derived from the β-globin gene. Cells co-transfected with the pMD L g/p RRE packaging vector and Rev expressed gag/pol whereas in the absence of Rev, no gag/pol was detected.

Figure 3:
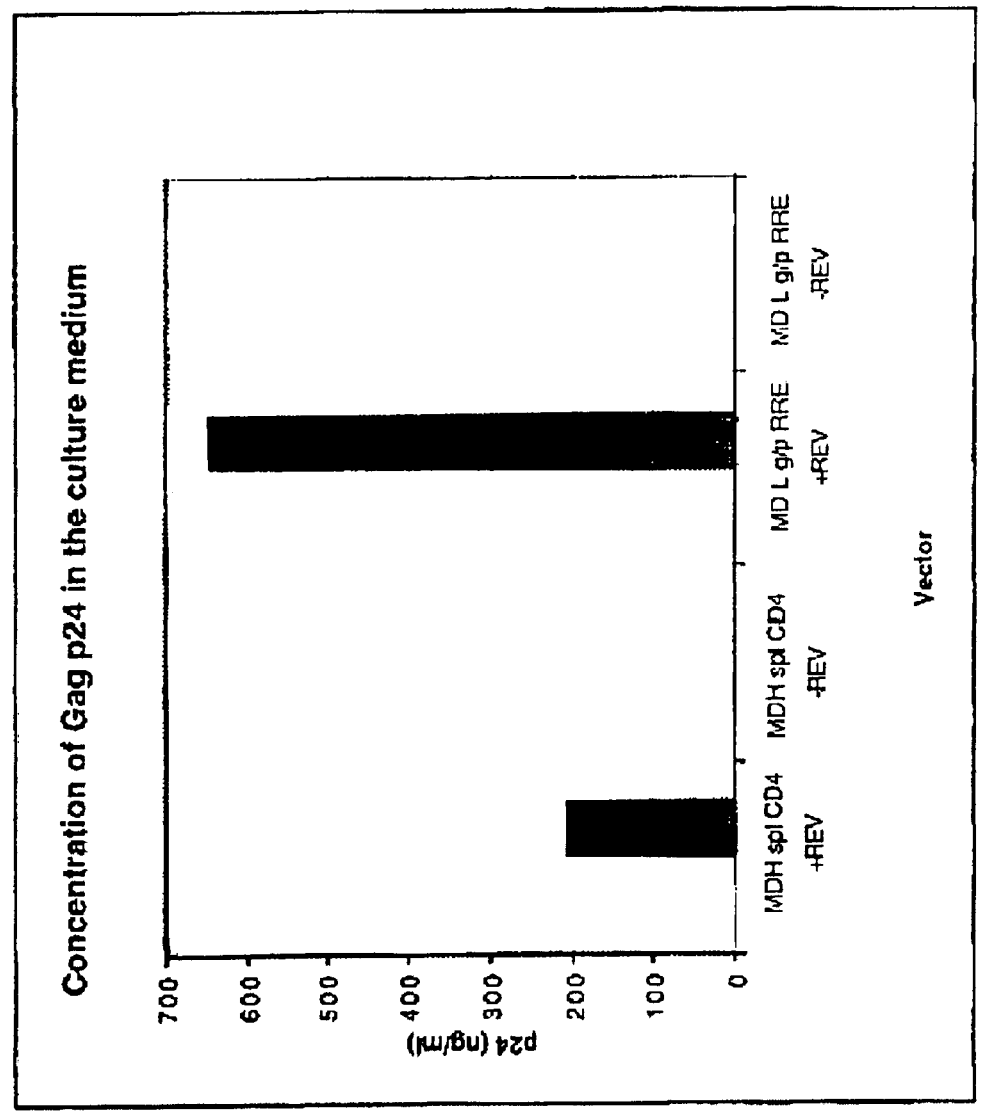
FIG. 3 is a graph depicting the amounts of p24, a product of the gag gene, in culture medium when cells containing a vector of the instant invention are propagated in the presence or absence of Rev. Two different vectors were used, MDH spl CD4 and MD L g/p RRE. In both vectors, the gag/pol genes are framed by splice donor and splice acceptor sites and thus p24 is expressed when Rev is present in the culture.

Expression of the gag/pol genes in the transfected 293T cells was analyzed by measuring the content of the gag gene product, p24, in the conditioned medium by immunocapture (DuPont). FIG. 3 shows the p24 concentration in the conditioned media of cells transfected with both packaging vectors in the presence and absence of HIV Rev. The Rev dependence of gag/pol expression for both plasmid is evident. The plasmid which contains the CD4 coding sequence expresses a very high level of p24 protein in the presence of Rev, similar to that obtained with the control plasmid.

Production of functional vector was analyzed by using the 293T conditioned medium to transduce the GFP gene into HeLa cells. HeLa cells were exposed to 10 μl of medium conditioned by cells transfected with the pMDH L g/p RRE Spl CD4 packaging vector or the pMD L g/p RRE packaging vector in the presence (a) and absence (b) of HIV Rev. Transduction experiments were carried out by plating $5 \times 10^4$ cells/well in 6-well plates the night prior to infection. The next day, frozen 293T conditioned medium was thawed and diluted 1:10, 1:100, 1:1000, and 1 ml of each dilution was used to infect the cells. Twenty hours after infection, fresh medium was added and 24 hours later, cells were analyzed by FACS for GFP expression.

The Rev-dependence of the transduction was evident for both plasmids. Only when Rev is expressed in vector producer cells do the target HeLa cells express GFP. Moreover, the infectivity (transducing units/ng p24) of vector produced by either plasmid is similar, indicating that the CD4-linked plasmid operates as efficiently as the control plasmid.

We claim:

1. A nucleic acid construct consisting of in operable linkage in the 5' to 3' direction;

(1) a promoter;

(2) a splice donor site;
(3) a gag/pol coding sequence;
(4) a Rev responsive element;
(5) a splice acceptor site; and
(6) a selectable marker coding sequence.

2. The nucleic acid construct of claim 1, wherein the splice acceptor site is that of the third exon of the HIV-1 tat and rev genes.

3. The nucleic acid construct of claim 1, wherein the splice donor site is the major 5' splice donor site of HIV.

4. A composition comprising:
   (a) a first expression cassette comprising the nucleic acid construct of claim 1; and
   (b) a second expression cassette comprising in operable linkage in the 5' to 3' direction:
       (1) a promoter; and
       (2) a nucleic acid encoding a factor which binds to element (4) of said first expression cassette, which on such binding regulates splicing at said sites (2) and (5) of said first expression cassette when an mRNA is transcribed from said first expression cassette.

5. The composition of claim 4, wherein the splice acceptor suite is that of the third exon of the HIV-1 tat and rev genes.

6. A composition comprising:
   (a) a first expression cassette comprising in operable linkage in the 5' to 3' direction:
       (1) a promoter;
       (2) a splice donor site;
       (3) a gag/pol coding sequence;
       (4) a Rev responsive element contiguous with;
       a splice acceptor site that is from the third exon of the HIV-1 tat and rev genes; and
       (5) a selective marker coding sequence; and
   (b) a second expression cassette comprising in operable linkage in the 5' to 3' direction:
       (1) a promoter; and
       (2) a nucleic acid encoding a factor which binds to element (4) of said first expression cassette, which on such binding regulates splicing at said sites (2) and (4) of said first expression cassette when an mRNA is transcribed from said first expression cassette.

7. The composition of claim 6, wherein the splice donor site of the first expression cassette is the major 5' splice donor site of HIV.

* * * * *